US007335472B2

(12) United States Patent
Mandrand et al.

(10) Patent No.: US 7,335,472 B2
(45) Date of Patent: Feb. 26, 2008

(54) METHOD FOR SIMULTANEOUSLY DETECTING HYBRIDIZATION REACTIONS AND IMMUNO-REACTIONS, AND ITS USES IN DIAGNOSIS

(75) Inventors: Bernard Mandrand, Villeurbanne (FR); Agnès Perrin, Lyons (FR); Alain Theretz, Ecully (FR)

(73) Assignee: Biomerieux, Marcy l'Etoile (FR)

( * ) Notice: Subject to any disclaimer, the term of this patent is extended or adjusted under 35 U.S.C. 154(b) by 413 days.

(21) Appl. No.: 10/515,495

(22) PCT Filed: Jun. 3, 2003

(86) PCT No.: PCT/FR03/01659

§ 371 (c)(1),
(2), (4) Date: Nov. 24, 2004

(87) PCT Pub. No.: WO03/104490

PCT Pub. Date: Dec. 18, 2003

(65) Prior Publication Data

US 2005/0227234 A1   Oct. 13, 2005

(30) Foreign Application Priority Data

Jun. 5, 2002   (FR) ................................. 02 06883

(51) Int. Cl.
*C12Q 1/68* (2006.01)
*C12N 15/11* (2006.01)
(52) U.S. Cl. .......................................... 435/6; 536/23.1
(58) Field of Classification Search ...................... None
See application file for complete search history.

(56) References Cited

U.S. PATENT DOCUMENTS

| 5,837,465 A | 11/1998 | Squirrell et al. ................ 435/6 |
| 5,849,545 A | 12/1998 | Henco et al. .............. 435/91.2 |

FOREIGN PATENT DOCUMENTS

| FR | 2 781 802 A1 | 2/2000 |
| FR | 2 816 711 A1 | 5/2002 |
| WO | WO 93/23565 A1 | 11/1993 |
| WO | WO 95/08000 A2 | 3/1995 |
| WO | WO 97/29206 A1 | 8/1997 |
| WO | WO 00/75644 A1 | 12/2000 |
| WO | WO 01/61040 A1 | 8/2001 |
| WO | WO 01/86296 A2 | 11/2001 |
| WO | WO 01/88511 A1 | 11/2001 |

OTHER PUBLICATIONS

Savoy et al, SPIE conference on Chemical Microsensors and Applications, SPIE vol. 3539 (Nov. 4, 1998).*
Ravindra Kumar et al.; "The First Analogues of LNA (Locked Nucleic Acids): Phosphorothioate-LNA and 2'-Thio-LNA"; *Bioorganic & Medicinal Chemistry Letters*; 8: pp. 2219-2222; 1998.

Michael Egholm et al.; "Peptide Nucleic Acids (PNA). Oligonucleotide Analogues with an Achiral Peptide Backbone"; *J. Am. Chem. Soc.*; 114: pp. 1895-1897; 1992.

M.T. Corasaniti et al.; "Evidence that the HIV-1 coat protein gp120 causes neuronal apoptosis in the neocortex of rat via a mechanism involving CXCR4 chemokine receptor"; *Neuroscience Letters*; 312: pp. 67-70; 2001.

A. Perrin et al.; "Immunomagnetic concentration of antigens and detection based on a scanning force microscopic immunoassay"; *Journal of Immunological Methods*; 224: pp. 77-87; 1999.

Jacques Chevalier et al.; "Biotin and Digoxigenin as Labels for Light and Electron Microscopy in Situ Hybridization Probes: Where Do We Stand?"; *The Journal of Histochemistry & Cytochemistry*; vol. 45 (4): pp. 481-491; 1997.

Greg T. Hermanson; "Nucleic Acid and Oligonucleotide Modification and Conjugation"; *Bioconjugate Techniques*; pp. 640-671; 1996.

James P. Gosling; "Enzyme Immunoassay: with and without Separation"; *Principles and Practice of Immunoassay*; $2^{nd}$ Edition; pp. 349-380; New York; 1997.

Larry Mole et al.; "Stabilities of Quantitative Plasma Culture for Human Immunodeficiency Virus, RNA, and p24 Antigen from Samples Collected in VACUTAINER CPT and Standard VACUTAINER Tubes"; *Journal of Clinical Microbiology*; vol. 32, No. 9: pp. 2212-2215; Sep. 1994.

Nanping Wu et al.; "Study on the Correlations of P24 antigen, HIV DNA, HIV RNA in 139 HIV Infected Cases"; *Zhonghua Weishengwuxue He Mianyixue Zazhi*; vol. 18, No. 5; 1998.

(Continued)

*Primary Examiner*—James Martinell
(74) *Attorney, Agent, or Firm*—Oliff & Berridge, PLC (57) ABSTRACT

The present invention relates to a method for simultaneously detecting hybridization reactions and immunoreactions in a sample which may contain target analytes consisting of at least one nucleic acid and of at least one other ligand that is different in nature, characterized in that it comprises the steps consisting in:

(i) depositing a known amount of volume of the sample diluted in a reaction buffer, onto a capture surface pre-coated with the partners for capturing said target analytes, said capture partners consisting of at least one nucleic acid probe and at least one antiligand, (ii) reacting at a temperature of between 15° C. and 60° C. and (iii) visualizing the hybridization reactions and immunoreactions thus obtained, and also to the use of this method for detecting diseases of infectious or metabolic origin or viral origin, for the industrial diagnosis of the presence of bacteria, and for identifying and/or quantifying biological molecules.

The invention also relates to the use of this method in diagnosis and the biological or diagnostic test kits that are useful for carrying out the method of the invention.

28 Claims, 2 Drawing Sheets

OTHER PUBLICATIONS

I. J. Koralnik et al.; "JC virus DNA load in patients with and without progressive multifocal leukoencephalopathy"; *Neurology*; vol. 52, No. 2: pp. 253-260; Jan. 15, 1999.

Jean-Jacques Toulmé et al.; "Les aptaméres: des ligands et des catalyseurs oligonucléotidiques obtenus par sélection in vitro"; *médecine/sciences*; 14: pp. 155-166; 1998.

* cited by examiner

SEQUENCE LISTING

<160> NUMBER OF SEQ ID NOS: 13

<210> SEQ ID NO 1
<211> LENGTH: 21
<212> TYPE: DNA
<213> ORGANISM: artificial sequence
<220> FEATURE:
<223> OTHER INFORMATION: Capture oligonucleotide C+

<400> SEQUENCE: 1
cgcttcgaca gcgacgtggg g                                            21

<210> SEQ ID NO 2
<211> LENGTH: 20
<212> TYPE: DNA
<213> ORGANISM: artificial sequence
<220> FEATURE:

```
<223> OTHER INFORMATION: Capture oligonucleotide C-

<400> SEQUENCE: 2
tatgaaactt atggggatac                                                    20

<210> SEQ ID NO 3
<211> LENGTH: 21
<212> TYPE: DNA
<213> ORGANISM: artificial sequence
<220> FEATURE:
<223> OTHER INFORMATION: Primer A

<400> SEQUENCE: 3
catgtgctac ttcaccaacg g                                                  21

<210> SEQ ID NO 4
<211> LENGTH: 21
<212> TYPE: DNA
<213> ORGANISM: artificial sequence
<220> FEATURE:
<223> OTHER INFORMATION: Primer B

<400> SEQUENCE: 4
ctggtagttg tgtctgcaca a                                                  21

<210> SEQ ID NO 5
<211> LENGTH: 27
<212> TYPE: DNA
<213> ORGANISM: artificial sequence
<220> FEATURE:
<223> OTHER INFORMATION: Primer SK431

<400> SEQUENCE: 5
tgctatgtca gttcccttg gttctct                                             27

<210> SEQ ID NO 6
<211> LENGTH: 30
<212> TYPE: DNA
<213> ORGANISM: artificial sequence
<220> FEATURE:
<223> OTHER INFORMATION: Primer SK462

<400> SEQUENCE: 6
agttggagga catcaagcag ccatgcaaat                                         30

<210> SEQ ID NO 7
<211> LENGTH: 33
<212> TYPE: DNA
<213> ORGANISM: artificial sequence
<220> FEATURE:
<223> OTHER INFORMATION: Capture probe C HIV

<400> SEQUENCE: 7
gagaccatca atgaggaagc tgcagaatgg gat                                     33

<210> SEQ ID NO 8
<211> LENGTH: 20
<212> TYPE: DNA
<213> ORGANISM: artificial sequence
<220> FEATURE:
<223> OTHER INFORMATION: Primer RC21

<400> SEQUENCE: 8
ctcccggggc actcgcaagc                                                    20
```

```
<210> SEQ ID NO 9
<211> LENGTH: 20
<212> TYPE: DNA
<213> ORGANISM: artificial sequence
<220> FEATURE:
<223> OTHER INFORMATION: Primer RC1

<400> SEQUENCE: 9
gtgtagccat ggcgttagta                                              20

<210> SEQ ID NO 10
<211> LENGTH: 26
<212> TYPE: DNA
<213> ORGANISM: artificial sequence
<220> FEATURE:
<223> OTHER INFORMATION: Capture probe C HCV

<400> SEQUENCE: 10
catagtggtc tgcggaaccg gtgagt                                       26

<210> SEQ ID NO 11
<211> LENGTH: 75
<212> TYPE: DNA
<213> ORGANISM: artificial sequence
<220> FEATURE:
<223> OTHER INFORMATION: HBV target

<400> SEQUENCE: 11
cccagtaaag ttccccacct tatgagtcca aggaattact aacattgaga ttcccgagat   60
tgagatcttc tgcga                                                   75

<210> SEQ ID NO 12
<211> LENGTH: 22
<212> TYPE: DNA
<213> ORGANISM: artificial sequence
<220> FEATURE:
<223> OTHER INFORMATION: Capture probe HBV

<400> SEQUENCE: 12
atctcgggaa tctcaatgtt ag                                           22

<210> SEQ ID NO 13
<211> LENGTH: 19
<212> TYPE: DNA
<213> ORGANISM: Artificial sequence
<220> FEATURE:
<223> OTHER INFORMATION: D HBV

<400> SEQUENCE: 13
tattccgact cataaggtg                                               19
```

METHOD FOR SIMULTANEOUSLY DETECTING HYBRIDIZATION REACTIONS AND IMMUNO-REACTIONS, AND ITS USES IN DIAGNOSIS

BACKGROUND

The present invention relates to a novel method for simultaneously detecting hybridization reactions and immunoreactions, and also to its use in therapeutic and industrial diagnosis and in the identification and/or quantification of biological molecules.

The diagnosis or the monitoring of pathologies most commonly requires hybridization detections and/or immunodetections. Thus, in the case of AIDS diagnosis, it may be necessary to investigate both the presence of the p24 protein, of the anti-viral envelope protein antibody and of the viral RNA, or of anti-p24 protein antibody and of the viral RNA.

The simultaneous detection of the hybridization reactions and immunoreactions under the same operating conditions and in the same reaction medium would make it possible to facilitate the diagnosis of pathologies requiring such a double detection.

The detection of the immunoreactions and of hybridization reactions using common parameters has already been studied in the prior art.

Thus, patent application WO 01/86296 describes a method designed for the simultaneous detection of a large number of analytes using a panel of markers specific for each analyte. However, this method does not describe the simultaneous detection both of hybridization reactions and of immunoreactions, and uses operating conditions for visualization that are different for each marker specific for each analyte.

Patent application WO 01/61040 also describes a method for simultaneously detecting analytes using semiconducting nanocrystals as detection markers. The reading of the hybridization reactions or immunoreactions is carried out by means of the variation in wavelength for the reading. However, the disadvantage of this method is that the sample to be analyzed must be divided up into several samples, such that each analyte to be studied is subjected to different operating conditions.

The methods of the prior art therefore have the drawbacks that simultaneous detection of hybridization reactions and of immunoreactions cannot take place under the same operating conditions and in the same reaction medium, such that the simultaneous detection is complex and expensive.

SUMMARY

The applicant has now developed a novel method for simultaneously detecting hybridization reactions and immunoreactions which overcomes the abovementioned drawbacks.

Thus, a subject of the invention is a method for simultaneously detecting hybridization reactions and immunoreactions in a sample which may contain target analytes consisting of at least one nucleic acid and of at least one other ligand that is different in nature, characterized in that it comprises the steps consisting in:

(i) depositing a known amount of volume of the sample diluted in a reaction buffer, onto a capture surface pre-coated with the partners for capturing said target analytes, said capture partners consisting of at least one nucleic acid probe and at least one antiligand, (ii) reacting at a temperature of between 15° C. and 60° C. and (iii) visualizing the hybridization reactions and immunoreactions thus obtained, and also the use of this method for detecting diseases of infectious, for example viral, and metabolic origin, for the industrial diagnosis of the presence of bacteria, and also for identifying and/or quantifying biological molecules.

Another subject of the invention consists of biological or diagnostic test kits that are useful for carrying out the method of the invention.

DETAILED DESCRIPTION OF THE EMBODIMENTS

The method of the invention is a method simple to carry out, which makes it possible, against all expectations, to detect, in a sample, under the same operating conditions, namely the reaction medium and temperature, the presence of target analytes consisting of at least one nucleic acid and of at least one other ligand that is different in nature. The presence of said target analytes is demonstrated by means of the visualization of hybridization reactions and of immunoreactions.

The term "hybridization reaction" is intended to mean any reaction between a capture nucleic acid and a target nucleic acid, and the term "immunoreaction" is intended to mean any reaction between a capture antiligand and a target ligand that is other than nucleic acid in nature.

The term "nucleic acid" is intended to mean oligonucleotides, deoxyribonucleic acids and ribonucleic acids, and derivatives thereof.

The term "oligonucleotide" denotes a chain of at least 2 nucleotides (deoxyribonucleotides or ribonucleotides, or both), that are natural or modified, capable of hybridizing, under suitable hybridization conditions, with an at least partially complementary oligonucleotide. The term "modified nucleotide" is intended to mean, for example, a nucleotide comprising a modified base and/or comprising a modification in terms of the internucleotide bond and/or in terms of the backbone. By way of example of a modified base, mention may be made of inosine, methyl-5-deoxycytidine, dimethylamino-5-deoxyuridine, diamino-2,6-purine and bromo-5-deoxyuridine. To illustrate a modified internucleotide bond, mention may be made of phosphorothioate, N-alkylphosphoramidate, alkylphosphonate and alkylphosphodiester bonds. Alpha-oligonucleotides such as those described in FR-A-2 607 507, LNAs such as phosphorothioate-LNA and 2'-thio-LNA described in Bioorganic & Medicinal Chemistry Letters, Volume 8, Issue 16, Aug. 18, 1998, pages 2219-2222, and the PNAs which are the subject of the article by M. Egholm et al., J. Am. Chem. Soc. (1992), 114, 1895-1897, are examples of oligonucleotides consisting of nucleotides whose backbone is modified.

The expression "ligand that is different in nature, other than nucleic acid in nature" is intended to mean any molecule that is different from a nucleic acid, capable of binding with a specific binding partner. This binding partner is called an antiligand when it consists of the capture partner. For reasons of convenience, the terms "ligand" and "antiligand" will be used hereinafter to denote any compound capable of an immunoreaction, but not of a hybridization reaction.

As a ligand, mention may be made, for example, of antigens, antibodies, polypeptides, proteins, haptens, sugars, enzymes and their substrates.

As an antiligand, mention may be made of the same examples as those regarding the ligands, and also lectins, cell receptors and aptamers.

The term "antigen" denotes a compound capable of being recognized by an antibody whose synthesis it has induced by means of an immune response.

The term "antibody" includes polyclonal and monoclonal antibodies, antibodies obtained by genetic recombination and antibody fragments.

The polyclonal antibodies can be obtained by immunization of an animal with at least one target antigen of interest, followed by recovery of the desired antibodies in purified form, by taking the serum of said animal, and separating said antibodies from the other serum constituents, in particular by affinity chromatography on a column to which is attached an antigen specifically recognized by the antibodies, in particular a target antigen of interest.

The monoclonal antibodies can be obtained by the hybridoma technique, the general principle of which is recalled below.

Firstly, an animal, generally a mouse (or cells in culture in the case of in vitro immunizations), is immunized with a target antigen of interest, for which the B lymphocytes are then capable of producing antibodies against said antigen. These antibody-producing lymphocytes are then fused with "immortal" myeloma cells (murine cells in the example) so as to produce hybridomas. From the heterogeneous mixture of the cells thus obtained, a selection of the cells capable of producing a particular antibody and of multiplying indefinitely is then carried out. Each hybridoma is multiplied in the form of a clone, each one resulting in the production of a monoclonal antibody whose properties of recognition with respect to the tumor antigen of interest may be tested, for example by ELISA, by one- or two-dimensional immuno-blocking, by immunofluorescence, or using a biosensor. The monoclonal antibodies thus selected are subsequently purified, in particular according to the affinity chromatography technique described above.

The antibody fragments are such that they conserve the function of binding with their binding or capture partner.

The term "polypeptide" is intended to mean a chain of at least two amino acids. The term "amino acids" is intended to mean the primary amino acids which encode proteins, the amino acids derived after enzymatic action such as trans-4-hydroxyproline and the amino acids that are natural but not present in proteins, such as norvaline, N-methyl-L-leucine, staline (Hunt S. in Chemistry and Biochemistry of the amino acids, Barett G C, ed., Chapman and Hall, London, 1985), the amino acids protected with chemical functions that can be used in solid-support synthesis or in liquid phase, and the unnatural amino acids.

The term "protein" includes holoproteins and heteroproteins, such as nucleoproteins, lipoproteins, phosphoproteins, metalloproteins and glycoproteins, both fibrous and globular.

The term "hapten" denotes nonimmunogenic compounds, i.e. compounds incapable by themselves of promoting an immune reaction by antibody production, but capable of being recognized by antibodies obtained by immunization of animals under known conditions, in particular by immunization with a hapten-protein conjugate. These compounds generally have a molecular mass of less than 3000 Da, and most commonly less than 2000 Da, and may be, for example, glycosylated peptides, metabolites, vitamins, hormones, prostaglandins, toxins or various medicinal products, nucleosides and nucleotides.

The enzymes and their substrates are well known to those skilled in the art. The use of an enzyme as a capture antiligand makes it possible to search for substrate analogs for the enzyme, in the sample tested.

The lectins are capable of recognizing sugars by a mechanism well known to those skilled in the art, as described in Biochemistry, 4th Edition, G. L. Zubay, 1998, The Mc Graw-Hill Companies, USA, Boston.

The receptors used as antiligands are surface proteins capable of binding with the envelope protein target ligand. Examples of such receptors include the CXCR4 chemokine receptor for the HIV gp120 envelope protein (Corananiti, M. T., 2001, Neuroscience Letters, 312(2), 67-70).

The aptamers are capture partners that are protein and nucleic acid in nature, the function of which is to act as antibodies and to bind to protein ligands (Toulmé, J. J. and Giege, R., 1998, Medecine Science, 14(2), 155-166).

The sample tested in the method of the invention may be either biological or industrial.

As a biological sample, mention may be made of any biological fluid capable of containing target analytes such as blood, lymph, cerebrospinal fluid, a throat swab, vaginal smears, and urine.

As an industrial sample, mention may be made of any sample originating from industry, for which a biological analysis is necessary. Samples originating from the food industry (ready-prepared meals, treated water) constitute an example of an industrial sample.

The reaction buffer in which the sample is diluted is an intermediate reaction buffer between a hybridization buffer and a buffer used in immunoreactions. It can be readily determined by those skilled in the art.

According to a particular embodiment, the reaction buffer has an ionic strength of between 0.4 and 1 M, has a pH of between 7 and 8, and contains a surfactant.

As a reaction buffer, mention may be made of buffers based on phosphate salts, sodium salts, lithium salts and HEPES, and as a surfactant, mention may be made of Tween 20, Tween 80 and Triton.

The originality of the invention therefore consists in the fact that it is possible to detect both hybridization reactions and immunoreactions in this reaction buffer.

The reaction temperature of the method of the invention is between 15 and 60° C. At a temperature below 15° C., the hybridization reactions risk being relatively nonspecific, in particular if the oligonucleotides are more than 8 bp in length, and at a temperature above 60° C., problems may be encountered in terms of the ligands and antiligands. Indeed, at these temperatures, some proteins are denatured and the hybridization reactions are only possible with large oligonucleotides, longer than 30 bp.

According to one embodiment, the reaction temperature is between 35 and 45° C., preferably between 37 and 41° C., the temperatures of 37 and 41° C. being more preferred.

The capture surface on which the sample to be tested is deposited can be any surface to which it is possible to attach nucleic acid probes and antiligands. As a capture surface, mention may be made of microwells, microplates, polymer surfaces, membranes, microscope slides, functionalized or unfunctionalized inorganic supports such as silica, glass, mica or quartz, metal surfaces such as gold and silver, and particles and microparticles, in particular magnetic particles and microparticles.

For the method of the invention, the capture surface is precoated with the partners for capture of said target analytes, namely nucleic acid probes and antiligands.

The capture partners can be deposited according to the method described in the applicant's patent application FR 00/14691 (FR 2 816 711), which is a method of deposition without contact that is particularly suitable for the 96-well microplate format. This method consists in ejecting calibrated nanodroplets through a nozzle, under the effect of a mechanical impact, onto the bottom of the wells of the microplate. At each impact, a drop whose diameter varies according to that of the nozzle, from 50 to 500 µm, approximately, is thus obtained.

The deposition of these partners can also be carried out manually using glass capillaries having an internal diameter in the region of about a hundred microns. In this case, the capillary must come into contact with the deposition surface in order for the deposition to take place, which results in a slight impact with the deposition surface.

The visualization of the hybridization reactions and immunoreactions can be carried out by any detection means, such as direct or indirect means.

In the case of direct detection, i.e. without the use of labeling, the hybridization reactions and immunoreactions are observed, for example, by plasmon resonance or by cyclic voltametry on an electrode bearing a conducting polymer.

In the case of indirect detection, i.e. via labeling, the labeling can be carried out either directly on the target analytes or via a binding partner specific for said target analytes, that is prelabeled.

The expression "binding partner specific for the target analytes" is intended to mean any partner capable of binding with the target analyte, and by way of examples, mention will be made of nucleic acids, antigens, antibodies, antibody fractions, proteins, haptens, oligonucleotides or polynucleotides, and enzyme substrates.

According to an embodiment in which the visualization of the hybridization reactions and immunoreactions is carried out by means of prelabeled binding partners specific for said target analytes, the method of the invention comprises the following additional step (i'), placed between step (i) and step (ii), consisting in:

(i') adding binding partners specific for said target analytes, which partners have been conjugated to labels beforehand.

According to another embodiment in which the visualization of the hybridization reactions and immunoreactions is also carried out by means of prelabeled binding partners specific for said target analytes, the method of the invention comprises the following two additional steps (ii') and (ii"), placed between step (ii) and step (iii), consisting in:

(ii') adding binding partners specific for said target analytes, which partners have been conjugated to labels beforehand, and (ii") reacting at a temperature of between 15° C. and 60° C.

Thus, in this case, the method of the invention comprises two reaction steps, one for the binding between the partners for capturing the target analytes and the target analytes (step (ii)), and the other between the capture partner/target analyte conjugate and the binding partner specific for the target analyte (step (ii")).

According to yet another embodiment, the visualization of the hybridization reactions is carried out by means of the prelabeling of the target analytes of the nucleic acid type, and the visualization of the immunoreactions is carried out by means of the labeling of the binding partners specific for said target analytes of the ligand type. Consequently, in this embodiment, since the target nucleic acids have been prelabeled, the only binding partners to be added in step (i') or (ii') are the partner(s) specific for the ligand, which has(have) been prelabeled.

The immunoreactions can also be detected according to a "competition" method. The ligand(s) which may be contained in the biological sample, which ligand(s) has(have) been prelabeled, is(are) then added to the reaction medium (steps (i') and (ii')), in place of the ligand-specific partner(s), which constitutes another embodiment of the invention. In this case, the detection signal is at a maximum in the absence of the ligand being sought, and then gradually decreases as the concentration of ligand being sought, which is not labeled, increases via the competition reaction.

The capture surface may be rinsed after the reaction steps (steps (ii) and/or (ii")) of each embodiment of the invention, in order to remove from the capture surface the molecules which have not reacted and the molecules that are weakly adsorbed, without specific interaction. Thus, the visualization of the hybridization reactions and immunoreactions are accordingly improved. This constitutes another embodiment of the invention.

As rinsing medium, use may be made, for example, of PBS-tween, as described by A. Perrin et al., in J. Immunological Methods, 1999, 224, 77-87.

The term "labeling" is intended to mean the attachment of a label capable of directly or indirectly generating a detectable signal. A nonlimiting list of these labels consists of:

enzymes which produce a signal that is detectable, for example, by colorimetry, fluorescence or luminescence, such as horseradish peroxidase, alkaline phosphatase, α-galactosidase or glucose-6-phosphate dehydrogenase, chromophors such as luminescent or dye compounds, radioactive molecules such as $^{32}P$, $^{35}S$ or $^{125}I$, fluorescent molecules such as fluorescein, rhodomine, alexa or phycocyanins, and particles such as gold particles or magnetic latex particles, or liposomes.

Indirect systems can also be used, such as, for example, by means of another ligand/antiligand couple. The ligand/antiligand couples are well known to those skilled in the art, and mention may be made, for example, of the following couples: biotin/streptavidin, hapten/antibody, antigen/antibody, peptide/antibody, sugar/lectin, and polynucleotide/sequence complementary to the polynucleotide. In this case, it is the ligand which carries the binding agent. The antiligand may be directly detectable by means of the labels described in the paragraph above, or may itself be detectable by means of a ligand/antiligand.

These indirect detection systems can result, under certain conditions, in an amplification of the signal. This signal amplification technique is well known to those skilled in the art, and reference may be made to the prior patent applications FR 98/10084 or WO-A-95/08000 by the applicant or to the article J. Histochem. Cytochem. 45:481-491, 1997.

The prelabeling of the target analytes of the nucleic acid type can be carried out by direct or indirect incorporation of label by means of a polymerase.

The labeling of the binding partners specific for the target analytes is widely known to those skilled in the art and is described, for example, by Greg T. Hermanson in Bioconjugate Techniques, 1996, Academic Press Inc, 525B Street, San Diego, Calif. 92101 USA.

According to the type of labeling of the conjugate used, such as for example using an enzyme, those skilled in the art will add reagents for visualizing the labeling.

Thus, according to one embodiment of the method of the invention, the substrate(s) specific for the label(s) is(are) added before step (iii) for visualizing the hybridization reactions and immunoreactions.

Such reagents are widely known to those skilled in the art and are described in particular in Principles and Practice of Immunoessay, $2^{nd}$ Edition, Edited by C. Price, D. J. Newman Stockton Press, 1997, 345 Park Avenue South, New York.

The elements labeled for the purposes of the method of the invention, namely the nucleic acid-specific binding partners, the ligand-specific binding partners, the target nucleic acids contained in the biological sample and the ligands which may be contained in the biological sample, can be labeled with different labels or with the same label, the second solution being preferred.

The hybridization reactions and immunoreactions detected by the method of the invention may be representative of the presence of a single disease. In this case, the capture partners applied to the capture surface are markers for the same disease, which constitutes an embodiment of the invention.

Thus for example, in the case of the early diagnosis of AIDS, it is possible to search for the presence both of the anti-p24 protein antibody and of the viral RNA. The capture partners present at the capture surface may therefore be the p24 protein, and a nucleic acid probe capable of a hybridization reaction with the viral RNA.

The hybridization reactions and immunoreactions detected by the method of the invention can also be representative of various diseases. In this case, the binding partners are markers for different diseases, which constitutes another embodiment of the invention. Thus, the method of the invention can be used for screening for, using a single biological sample, under the same operating conditions and at the same time, several different diseases demonstrated either by means of the detection of a nucleic acid, or by means of the detection of a ligand of another nature. This method may, for example, be useful in analyzing blood derived from a donation, before transfusion, in which it is desired to verify that pathogens are not present.

The diseases which can be detected by means of the method of the invention are all diseases for which at least one target analyte and capture partner couple capable of interaction is known.

These diseases may be of infectious, namely viral or bacterial, origin, such as AIDS or the forms of hepatitis, or else they may be metabolic, such as hyperthyroidism or diabetes.

Thus, another subject of the invention consists of the use of the method of the invention, for detecting diseases of infectious or metabolic origin.

Yet another subject of the invention consists of the use of the method of the invention in the industrial diagnosis of the presence of bacteria. Indeed, the demonstration of the presence of bacteria in industry, in particular listeria or salmonellae in the food industry, can be carried out by detection of hybridization reactions (detection of bacterial DNA or RNA) and immunoreactions (detection of bacterial proteins).

Another subject of the invention also consists of the use of the method of the invention, for identifying and/or quantifying biological molecules. Indeed, when many different capture partners are used, demonstrating numerous different biological molecules, the method of the invention makes it possible to identify which molecule(s) is(are) present in the sample. Similarly, when a large number of capture partners, but with a small number of differences in nature, is used, the method of the invention makes it possible to quantify the biological molecules present in the sample, which can result in standard profiles for a pathology or for an environmental state being defined.

Another subject of the invention consists of the use of the method of the invention, for simultaneously detecting the transcriptome and the proteome of a cell or of an organism. The simultaneous detection of all the RNA (transcriptome) and of all the proteins (proteome) of a cell or of an organism thus makes it possible to demonstrate a potential dysfunction of overexpression of the proteins relative to the RNAs present, and vice versa.

In order to carry out the method of the invention, kits are available, consisting of at least one of the following elements:
  a capture surface,
  partners for capturing the target analytes consisting of at least one nucleic acid probe and at least one other antiligand that is different in nature,
  a reaction buffer,
  optionally, partners specific for the target ligands, that are prelabeled, or prelabeled ligands which may be contained in the sample to be tested, and
  optionally, partners specific for the target nucleic acids.

These kits, which can be described as biological test kits when the sample tested is industrial, or diagnostic test kits when the sample tested is biological, constitute another embodiment of the invention.

BRIEF DESCRIPTION OF THE DRAWINGS

The present invention will be understood more fully from the following examples, given only by way of nonlimiting illustration, and also from the attached FIGS. 1 and 2, in which:

FIG. 1 represents two graphs showing, firstly, the evolution of the fluorescence demonstrating the immunoreactions between the p24 protein/VEMA polymer capture partner and the anti-p24 protein antibody present in human sera, as a function of the dilution of the sera (FIG. 1A) and showing, secondly, the evolution of the fluorescence representative of the hybridization reactions, or of an absence of such reactions, where appropriate, between the nucleic acid probe capture partners C+ (capable of reacting with the HIV virus DNA target) and C− (incapable of reacting with the HIV virus DNA target) and the HIV virus DNA target, as a function of the dilution of the PCR product (FIG. 1B)

EXAMPLE 1

Preparation of the Capture Surfaces for the Detection of Hybridization Reactions and Immunoreactions for Demonstrating the Presence of the HIV Virus in a Patient 1.1 Preparation of the Capture Partner Capable of Recognizing Anti-p24 Protein Antibodies A solution of maleic anhydride vinyl ether polymer MAVE-67 (67 000 g/mol) at 1 g/l in a 90/10 (V/V) mixture of DMSO (dimethyl sulfoxide)/water was prepared in a flask. The mixture was left to incubate for 48 h at 37° C. 36 µg of recombinant p24 protein (pmR K24H, bioMérieux, Marcy l'Etoile, France) was then mixed with 100 µl of the polymer solution. The mixture was left to incubate for 3 h at 37° C.

1.2 Preparation of the Capture Partner Capable of Recognizing the DNA Target Amplified from the HIV Virus RNA Each of the following two oligonucleotides, C+ capable of hybridization with the DNA target and C– incapable of such a hybridization, was diluted to a concentration of 10 µM in 3+PBS buffer (0.45 M sodium chloride, 0.15 M sodium phosphate, pH 6.8)-EDTA 10 mM:

```
                                              (SEQ ID NO: 1)
C+: NH₂-CGC TTC GAC AGC GAC GTG GGG;

and (SEQ ID NO: 2)
C-: NH₂-TAT GAA ACT TAT GGG GAT AC.
```

1.3 Preparation of the Capture Surfaces 4 spots were deposited without contact, according to the method described in patent application FR 00/14691 as recalled above, in each well of a microtitration plate (Nunc Maxisorb). Two spots consisted of the p24 protein-MAVE polymer conjugates, one of the spots consisted of the C+ probe and one consisted of the C– probe.

After deposition of the spots, the plate was immediately placed in a chamber at 4° C. for 2 h, and was then incubated for 30 min at 60° C.

EXAMPLE 2

Preparation and Specific Capture of the Target Analytes 2.1 Preparation of the Target Analytes The DNA targets (200 bp) were produced by RT-PCR from part of a viral gene extracted from cell culture. They were biotinylated using the primers A and B below, labeled with biotin in the 5' position:

```
                                              (SEQ ID NO: 3)
Primer A: CAT gTg CTA CTT CAC CAA Cgg;

and (SEQ ID NO: 4)
Primer B: CTg gTA gTT gTg TCT gCA CAA.
```

These targets were denatured just before their introduction, by incubation with the same volume of 0.2N sodium hydroxide for 5 min at ambient temperature.

Various human sera, for which the presence or absence of anti-p24 protein antibodies have been tested beforehand by conventional methods, were diluted to 1/500 in a reaction buffer A, having a pH of 7, consisting of: 0.1 M sodium phosphate, 0.5 M sodium chloride, 0.65% tween 20, 0.014% salmon DNA and 2% PEG 4000.

2.2 Specific Capture of the Target Analytes

30 µl of diluted patient serum, 30 µl of reaction buffer A and 3 µl of denatured DNA target were mixed and this mixture was deposited in each well. It was left to react for 1 h at 37° C. The wells were then rinsed with a 50 mM sodium phosphate buffer containing 0.15 M sodium chloride and 0.05% tween 20 (PBS-tween).

EXAMPLE 3

Detection of the Hybridization Reactions and Immunoreactions

The following mixture was deposited in each well: 30 µl of reaction buffer A, 10 ng of a peroxidase-conjugated goat anti-human antibody (Jackson ImmunoResearch), 0.07 pmol of an oligonucleotide complementary to the ADN target, thus making it possible to sandwich said target between the capture probe immobilized at the bottom of the plate and the detection probe. This oligonucleotide was prelabeled in the 5' position with peroxidase. The reaction was left to occur for 1 h at 37° C. The wells were then rinsed with PBS-tween.

30 µl of a colorimetric precipitating substrate for peroxidase (TMB, bioFX) were then added to each well. The visualization takes place for 20 minutes. The substrate was then removed by pipetting and the optical density of each of the spots was measured using a microscope (Zeiss Axioplan2) connected to a CCD camera (Spot) and equipped with image processing software (Image Pro+, Soft Imaging). The software makes it possible to translate the signal intensity of each spot into a digital value of between 0 (black, no signal) and 255 (white, saturating signal).

By way of comparison, the procedures described above were repeated, but the DNA target was omitted in order to test the specificity of hybridization, or sera devoid of virus (HIV–) were used.

The results obtained are given in table 1 below.

TABLE 1

| Serum | Presence of the DNA target | Intensity of the spot C+ | Intensity of the spot C– | Intensity of the spot P24-MAVE |
|---|---|---|---|---|
| HIV+ | Yes | 103 | 48 | 115 |
| HIV– | Yes | 108 | 45 | 45 |
| HIV+ | No | 47 | 45 | 109 |
| HIV– | No | 46 | 51 | 48 |

The results above show that the specificity of the reaction is entirely satisfactory. The presence of DNA targets does not impair the recognition immunoreaction between P24 antigen and anti-P24 antibody. On the contrary, hybridization of the DNA targets on the nucleic acid probe spots is possible in the presence of antibodies in the medium. The presence of one or other of the analytes does not, either, generate an undesirable background noise. The C– spot is never detected, likewise for the HIV– sera.

EXAMPLE 4

Quantitative and Qualitative Determination of the Detection According to the Method of the Invention The procedure described in Examples 1 and 2 was repeated, except that the concentration of DNA target and the dilution of the HIV+ serum were varied.

The detection of the hybridization reactions and immunoreactions was then carried out as follows:

The following mixture was deposited in each well: 30 µl of reaction buffer A, 10 ng of an alkaline phosphatase-conjugated goat anti-human antibody (Jackson ImmunoResearch) and 25 ng of alkaline phosphatase-labeled streptavidin (Sigma). The mixture was left to react at 1 h for 37° C. The wells were then rinsed with PBS-tween.

30 µl of a fluorescent substrate for alkaline phosphatase (ECF, Amersham, ready-to-use) were then added to each well. The visualization takes place for 5 min, and then the substrate was removed by pipetting and the fluorescence intensity of each of the spots was measured as indicated in Example 3 above.

Figure 1A:
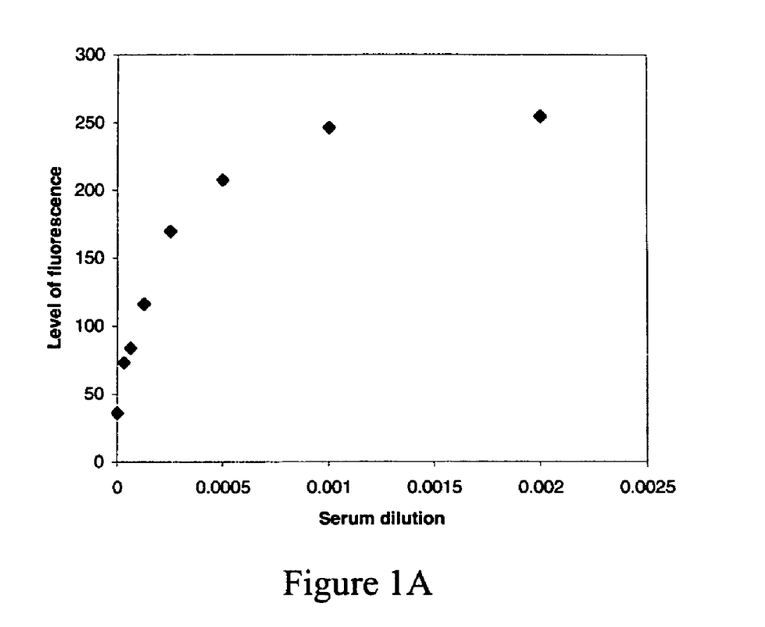
Figure 1B:
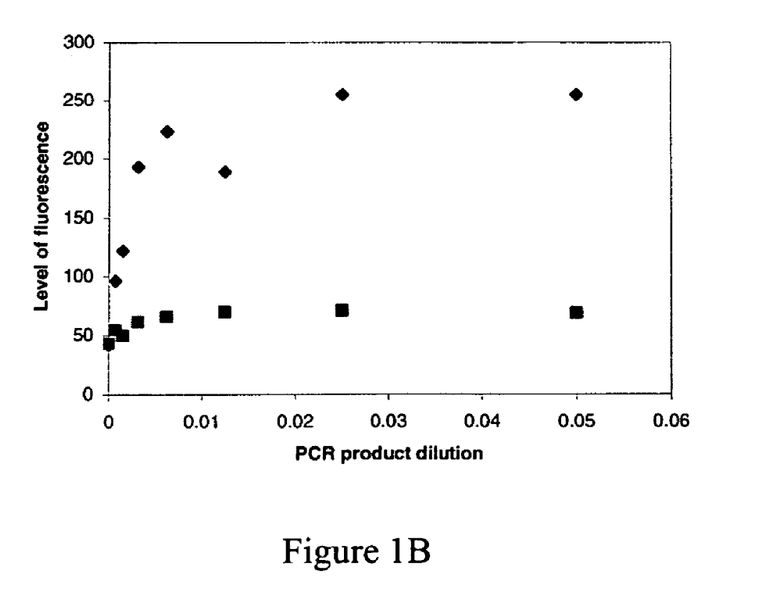

The results showing the level of fluorescence relative to the dilution of the serum or of the PCR product are represented in FIGS. 1A and 1B. For clarity reasons, the signals measured on the p24 protein-MAVE polymer conjugate spots were reported in FIG. 1A and those measured on the C+ spots (diamonds) and C− spots (squares), in the same well, were reported in FIG. 1B.

In FIG. 1A, a linear increase in the fluorescence signal is observed as a function of the concentration of serum in the well, and reaches a plateau for dilutions of less than 1/1000. It is thus possible to perform quantitative assays by means of this invention. The detection limit is estimated, according to a statistical method, at 0.00001, which corresponds to a serum dilution of 1/100 000. This high sensitivity allows early detection of the sera conversion subsequent to an HIV infection.

In FIG. 1B, a similar profile to that observed with the cascade dilutions of serum is obtained. The fluorescence signal increases as a function of the concentration of DNA target on the specific spot C+ (diamonds). On the other hand, the signal remains stable, similar to its level measured in the absence of target, on the C− spot which cannot be hybridized with the target (square). The detection limit is estimated at 0.00007, i.e. a dilution of the PCR product of 1/14 000.

EXAMPLE 5

Influence of the Modification of the Reaction Temperature and Buffer

The procedure of example 4 was repeated, except that reaction buffer B, having a pH of 7.5, consisting of: 160 mM HEPES, 0.5 M lithium chloride and 0.05% tween 20, was also used and the temperature was modified so that it was equal to 41° C.

In this experiment, the serum contained the virus (HIV+) and the target not recognizing the viral DNA (C−) was absent.

The results are given in table 2 below.

TABLE 2

| Temperature | Reaction buffer | Signal of the C+ spot | Signal of the P24-MAVE spot |
|---|---|---|---|
| 37° C. | A | 2.1 | 3.8 |
| 37° C. | B | 1.8 | 2.7 |
| 41° C. | A | 1.6 | 3.6 |
| 41° C. | B | 1.3 | 1.8 |

EXAMPLE 6

Simultaneous Detection of Viral Infections Caused by the HIV, HBV and HCV Viruses in a Detection Chip 6.1 Biological Tools for Assaying Combined Nucleic Acid and Protein Parameters 6.1.1 Hybridization Reactions HIV RNA targets obtained from Ambion (Austin, Tex., USA) were used. The biotinylated primers (SK431 TGC-TATGTCAGTTCCCCTTGGTTCTCT (SEQ ID NO: 5) and SK462 AGTTGGAGGACATCAAGCAGCCATGCAAAT (SEQ ID NO: 6)) and the aminated capture probes for capturing the PCR products ($C_{HIV}$: GAGACCATCAAT-GAGGAAGCTGCAGAATGGGAT (SEQ ID NO: 7) were synthesized by Eurogentec (Seraing, Belgium).

The HCV virus RNAs were extracted from sera of chronic patients using the Nucleospin RNA Virus Kit (Macherey-Nagel, Hoerdt, France) and amplified by RT-PCR with biotinylated primers (RC21: CTCCCGGGGCACTCG-CAAGC (SEQ ID NO: 8) and RC1: GTGTAGCCATG-GCGTTAGTA (SEQ ID NO: 9)) (Roque Afonso A.M., 2000, Journal of Virological Methods, 86, 55-60). The sequence of the aminated HCV capture probe is $C_{HCV}$ (CATAGTGGTCTGCGGAACCGGTGAGT (SEQ ID NO: 10)). The HIV and HCV RNAs were amplified by RT-PCR under the following conditions using the Access kit from Promega (Madison, Wis., USA): 1×AMV/Tfl reaction buffer, 1.8 mM MgSO$_4$, 0.2 mM dNTP, 1 µM of primers, 1USI of AMV reverse transcriptase and 5USI of Tfl DNA polymerase; cycle RT 48° C., 45 min; 35 PCR cycles (94° C., 30 s; 60° C., 1 min; 68° C., 2 min); final extension at 68° C. for 7 min.

The amplicons were analyzed on an agarose+ethidium bromide gel. The concentrations of the amplified products were evaluated using a mass ladder (Eurogentec) (46 nM for the HIV amplicons, 23 nM for the HCV amplicons).

A single-stranded synthetic target derived from the HBV gene (74 bp) (CCCAGTAAAGTTCCCCACCTTAT-GAGTCCAAGGAATTACTAATTACTAA-CATTGATTCCCCSTTGAGATTCCC GAGAT-TGAGATCTTCTGCGA (SEQ ID NO: 11)), an aminated capture probe ($C_{HBV}$: ATCTCGGGAATCTCAATGTTAG (SEQ ID NO: 12)) and a biotinylated detection probe ($D_{HBV}$: TATTCCGACTCATAAGGTG (SEQ ID NO: 13)), both complementary to the HBV target, were synthesized at Eurogentec.

6.1.2 Immunoreactions

The HCV core protein (HCV core) and also the HIV envelope protein (gp160) were produced by the applicant. Two different HBV surface antigens (HBAgs) were used, namely a subtype Ay antigen (Hytest, Turku, Finland) and a Cliniqa plasma subtype Ad antigen (Fallbrook, Calif., USA).

Two mouse antibodies nonspecific for this study were used, namely an anti-TSH antibody ($NSP_1$) and an anti-HCG antibody ($NSP_2$), so as to be sure of the specificity of the assays.

The HIV, HBV and HCV human sera were provided by the hospitals of Lyon.

The alkaline phosphatase-labeled anti-human goat IgG conjugates were provided by Jackson Immunoresearch (West Grove, Pa., USA) and the alkaline phosphatase-labeled streptavidin comes from Sigma (St Quentin, France).

6.2 Preparation of the Detection Chip and Biological Assay Protocol 6.2.1 Deposition of the Capture Partners The oligonucleotides were diluted to 10 μM in a reaction buffer for adsorption of the oligonucleotides (150 mM phosphate, 450 mM NaCl, 1 mM EDTA; pH 7.4).

The nonspecific IgGs were diluted to 50 μg/ml in a 50 mM carbonate buffer, pH 9.3.

The gp160, HBAg and HCV core proteins were diluted to 10 μg/ml in PBS.

Figure 2:
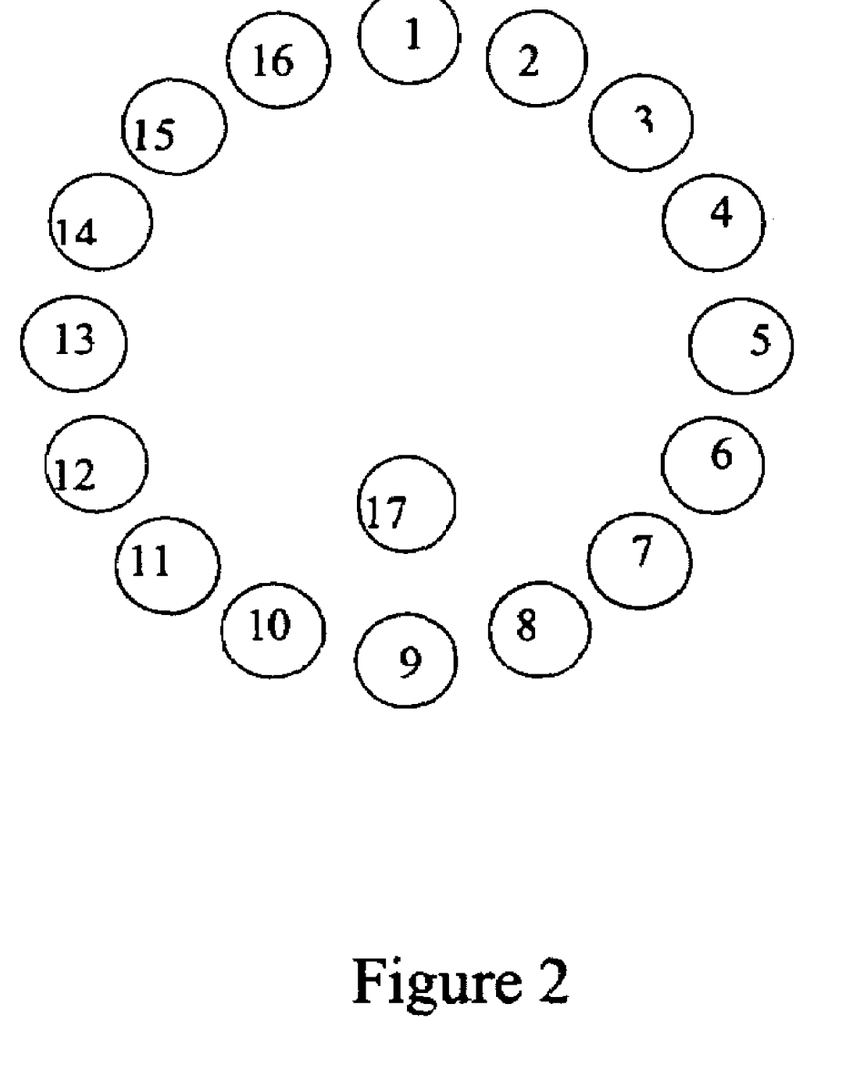
FIG. 2 represents the depositing plan for a multidose detection chip having 17 wells each comprising the capture partners in duplicate, with:
  in wells 1, 9 and 17: nucleic acid capture partners for the HIV virus ($C_{HIV}$),
  in wells 3 and 11: nucleic acid capture partners for the hepatitis B virus HBV ($C_{HBV}$),
  in wells 7 and 15: nucleic acid capture partners for the hepatitis C virus HCV ($C_{HCV}$),
  in wells 5 and 13: protein capture partners for the HIV virus (gp160 envelope protein),
  in wells 4 and 12: protein capture partners for the HCV virus (core protein),
  in wells 8 and 16: protein capture partners for the HBV virus (2 different HBAg surface antigens per well), and
  in wells 2, 6, 10 and 14: protein capture partners not specific for this study, namely an anti-TSH antibody (NSP1, wells 2 and 10) and an anti-HCG antibody (NSP2, wells 6 and 14).

The deposits were made using the Biochip Arrayer device (Perkin Elmer, Boston, USA). 16+1 spots were deposited in the form of a spot, in duplicate, on a circular format, in white microtitration plates (Greiner, Longwood, USA) (FIG. 2).

After deposition and incubation under controlled conditions of temperature (10° C.) and of humidity (50%), the plates were washed (PBS-tween 0.05%), dried, and stored at 4° C.

6.2.2 Capture of the Nucleic Acid Targets and of the Antibodies

The various analyte combinations below were used:
I: HBV targets,
II: HIV targets
III: HBV serum
IV: HIV serum
V: HBV+HIV targets
VI: HBV+HIV+HCV targets
VII: HBV+HIV+HCV targets+HBV serum
VIII: HBV+HIV+HCV targets+HBV serum+HIV serum To do this, the following were introduced into each well: 1.5 μl of HIV or HCV amplification product, denatured beforehand with 1.5 μl of 0.2N sodium hydroxide; 3 μl of synthetic HBV DNA at 10 nM; 1 μl of human serum diluted to 1/10. The volume was made up to 30 μl with reaction buffer (0.1 M $Na_2HPO_4/NaH_2PO_4$; 0.5 M NaCl; 0.65% tween 20; 2% PEG 4000; pH 7) and the solutions were incubated for 1 h at 37° C., and were then rinsed with a PBS-tween 0.05% mixture.

6.2.3 Detection

The plates were incubated with a 0.2 μM solution of $D_{HBV}$ (HBV detection) for 30 minutes at 37° C., and were then rinsed. They were then incubated in the presence of a solution of streptavidin-alkaline phosphatase (0.5 μg/ml) and of alkaline phosphatase-labeled anti-human goat antibodies (μg/ml). The plates were then washed with PBS-tween 0.05%, and a precipitating substrate for alkaline phosphatase was then added to each well (BM purple, Roche, Basel, Switzerland). The plates were photographed using a CCD camera coupled to image analysis software, which makes it possible to determine the mean level of gray associated with each spot.

The results are given in table 3 below.

TABLE 3

| Analyte combination | Expected position of the spots | Obtained position of the spots | Level of gray associated with each of the analytes (a.u.) |
|---|---|---|---|
| I | 3, 11 | 3, 11 | 34 935 |
| II | 1, 9, 17 | 1, 9, 17 | 38 144 |
| III | 8, 16 | 8, 16 | 33 664 |
| IV | 5, 13 | 5, 13 | 12 480 |
| V | 3, 11 | 3, 11 | 43 605 |
|   | 1, 9, 17 | 1, 9, 17 | 49 470 |
| VI | 3, 11 | 3, 11 | 43 350 |
|   | 1, 9, 17 | 1, 9, 17 | 48 832 |
|   | 7, 15 | 7, 15 | 14 917 |
| VII | 3, 11 | 3, 11 | 36 465 |
|   | 1, 9, 17 | 1, 9, 17 | 42 712 |
|   | 7, 15 | 7, 15 | 11 857 |
|   | 8, 16 | 8, 16 | 45 772 |
| VIII | 3, 11 | 3, 11 | 34 807 |
|   | 1, 9, 17 | 1, 9, 17 | 40 290 |
|   | 7, 15 | 7, 15 | 11 730 |
|   | 8, 16 | 8, 16 | 42 840 |
|   | 5, 13 | 5, 13 | 12 240 |

The relevant spots appear as a function of the nature of the analyte incubated, which shows that the hybridization reactions and immunoreactions take place under the same operating conditions, in particular in the same buffer and at the same temperature, even when the capture partners are markers for different diseases.

The invention claimed is:

1. A method for simultaneously detecting hybridization reactions and immunoreactions in a sample which may contain target analytes comprising at least one nucleic acid and at least one ligand other than a nucleic acid, comprising:
   (i) depositing a known volume of the sample diluted in a reaction-buffer onto a capture surface pre-coated with capture partners for capturing said target analytes, wherein said capture partners are at least one nucleic acid probe and at least one antiligand,
   (ii) reacting at a temperature of between 15° C. and 60° C., and
   (iii) visualizing the hybridization reactions and immunoreactions thus obtained,
   wherein at least one substrate for visualizing the hybridization reactions and immunoreactions is added before step (iii).

2. The method as claimed in claim 1, further comprising the following step placed between step (i) and step (ii):
   (i') adding labeled binding partners that bind at least one of said target analytes.

3. The method as claimed in claim 2, wherein the target nucleic acid in the sample are prelabeled, and the labeled binding partners added in step (i') consist of labeled binding partners that bind the target ligand.

4. The method as claimed in claim 2, wherein the labeled binding partners that bind nucleic acids and binding partner that binds a ligand are labeled with the same label.

5. The method as claimed in claim 1, further comprising the following steps placed between step (ii) and step (iii):
   (ii') adding labeled binding partners that bind at least one of said target analytes and
   (ii") reacting at a temperature of between 15° C. and 60° C.

6. The method as claimed in claim 3, wherein the target nucleic acid in the sample are prelabeled, and the labeled binding partners added in step (ii') consists of labeled binding partners that bind the target ligand.

7. The method as claimed in claim 5, wherein the capture surface is rinsed after step (ii) and/or (ii").

8. The method as claimed in claim 1, further comprising an additional step, placed between step (i) and step (ii):
   (i') adding at least one prelabeled ligand that corresponds to a ligand other than a nucleic acid that may be contained in the sample.

9. The method as claimed in claim 8, wherein target nucleic acid contained in the biological sample has been prelabeled.

10. The method as claimed in claim 8, wherein step (i') further comprises adding prelabeled binding partner that binds target nucleic acid.

11. The method as claimed in claim 1, wherein the capture surface is rinsed after step (ii).

12. The method as claimed in claim 1, wherein the reaction temperature is between 35° and 45° C.

13. The method as claimed in claim 12, wherein the reaction temperature is between 37° and 41° C.

14. The method as claimed in claim 13, wherein the reaction temperature is 37° C. or 41° C.

15. The method as claimed in claim 1, wherein the reaction buffer has an ionic strength of between 0.4 and 1 M, has a pH of between 7 and 8, and contains a surfactant.

16. The method as claimed in claim 1, wherein the capture partners are markers for the same disease.

17. The method as claimed in claim 1, wherein the capture partners are markers for different diseases.

18. The method as claimed in claim 1, for detecting diseases of infectious or metabolic origin.

19. The method as claimed in claim 18, for detecting diseases of viral origin.

20. The method as claimed in claim 1, for the industrial diagnosis of the presence of bacteria.

21. The method as claimed in claim 1, for identifying and/or quantifying biological molecules.

22. The method as claimed in claim 1, for simultaneously detecting the transcriptome and the proteome of a cell or of an organism.

23. The method as claimed in claim 1, further comprising the following steps placed between step (ii) and step (iii):
   (ii') adding at least one prelabeled ligand that corresponds to a ligand that may be contained in the sample, and
   (ii") reacting at a temperature of between 15° C. and 60° C.

24. The method as claimed in claim 23, wherein a target nucleic acid in the sample is prelabeled.

25. The method as claimed in claim 23, wherein step (ii') further comprises adding prelabeled binding partner specific for the target nucleic acid.

26. A diagnostic kit, comprising:
   a capture surface,
   partners for capturing target analytes, the capture partners comprising at least one nucleic acid probe and at least one antiligand other than a nucleic acid,
   a reaction buffer, and
   binding partners that bind target ligands.

27. The diagnostic kit as claimed in claim 26, further comprising a prelabeled ligand that corresponds to a ligand other than a nucleic acid that may be contained in a sample to be tested with the kit.

28. The diagnostic kit as claimed in claim 26, further comprising binding partners that bind target nucleic acids.

* * * * *